(12) United States Patent
Camps et al.

(10) Patent No.: US 6,397,108 B1
(45) Date of Patent: May 28, 2002

(54) SAFETY ADAPTOR FOR TEMPORARY MEDICAL LEADS

(75) Inventors: Antoine N. J. M. Camps, Eys/Wittem (NL); Farid Moumane, Trelon (FR); Jean Robinet, Anor (FR); Bernardt Cuisset, Boulogne S/Helpe (FR); Gert Landheer, Geleen (NL); Benoit Deruyver, Avesnes S/Helpe (FR)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 09/542,698

(22) Filed: Apr. 3, 2000

(51) Int. Cl.[7] .............................................. A61N 1/00
(52) U.S. Cl. ........................... 607/115; 607/1; 128/897
(58) Field of Search ........................ 607/1, 115, 116; 128/897; 600/372

(56) References Cited

U.S. PATENT DOCUMENTS

| | | |
|---|---|---|
| 3,035,583 A | 5/1962 | Hirsch et al. |
| 3,244,174 A | 4/1966 | Wesbey et al. |
| 3,416,533 A | 12/1968 | Fisher et al. |
| 3,664,347 A | 5/1972 | Harmjanz ................ 128/404 |
| 3,949,756 A | 4/1976 | Ace ............................ 128/339 |
| 4,010,756 A | 3/1977 | DuMont et al. ........... 128/404 |
| B14,010,756 A | 3/1977 | DuMont et al. ........... 128/404 |
| 4,054,144 A | 10/1977 | Hoffman et al. .......... 128/339 |
| 4,245,642 A | 1/1981 | Skubitz et al. ......... 128/419 P |
| 4,338,947 A | 7/1982 | Williams .................... 128/642 |
| 4,341,226 A | 7/1982 | Peters ......................... 128/784 |
| 4,442,840 A | 4/1984 | Wojciechowicz, Jr. ... 128/419 P |
| 4,444,207 A | 4/1984 | Robicsek ..................... 128/785 |
| 4,466,441 A | 8/1984 | Skubitz et al. ......... 128/419 P |
| 4,530,368 A | 7/1985 | Saulson et al. ............ 128/784 |
| 4,541,440 A | 9/1985 | Parsonnet ................... 128/785 |
| 4,553,554 A | 11/1985 | Lemole ...................... 128/784 |
| 4,630,617 A | 12/1986 | Ritter et al. ............... 128/784 |
| 4,633,880 A | 1/1987 | Osypka et al. ............. 128/642 |
| 4,693,258 A | 9/1987 | Osypka et al. ............. 128/783 |
| 4,972,833 A | 11/1990 | Wildon .................... 128/419 P |
| 5,217,027 A | 6/1993 | Hermens .................... 128/784 |
| 5,241,957 A | 9/1993 | Camps et al. ............... 607/119 |
| 5,314,463 A | 5/1994 | Camps et al. ............... 607/129 |
| 5,334,045 A | 8/1994 | Cappa et al. ............... 439/506 |
| 5,350,419 A | 9/1994 | Bendel et al. .............. 607/132 |
| 5,423,876 A | 6/1995 | Camps et al. ............... 607/116 |
| 5,557,210 A | 9/1996 | Cappa et al. ............... 324/539 |
| 5,679,022 A | 10/1997 | Cappa et al. ............... 439/502 |
| 5,782,892 A | 7/1998 | Castle et al. .................. 607/37 |
| 5,792,217 A | 8/1998 | Camps et al. ............... 607/119 |
| 5,871,528 A | 2/1999 | Camps et al. ............... 607/119 |
| 5,931,861 A | 8/1999 | Werner et al. .............. 607/115 |

Primary Examiner—Carl Layno
(74) Attorney, Agent, or Firm—Thomas F. Woods; Thomas G. Rerry

(57) ABSTRACT

Safety adaptors for connecting external medical devices to lead connector elements of temporary medical leads extending percutaneously into a patient's body are disclosed. The safety adaptors comprise a first member attached to but movable in respect of a second member. An elongated bore receives a lead proximal end segment and includes the lead connector elements.

50 Claims, 9 Drawing Sheets

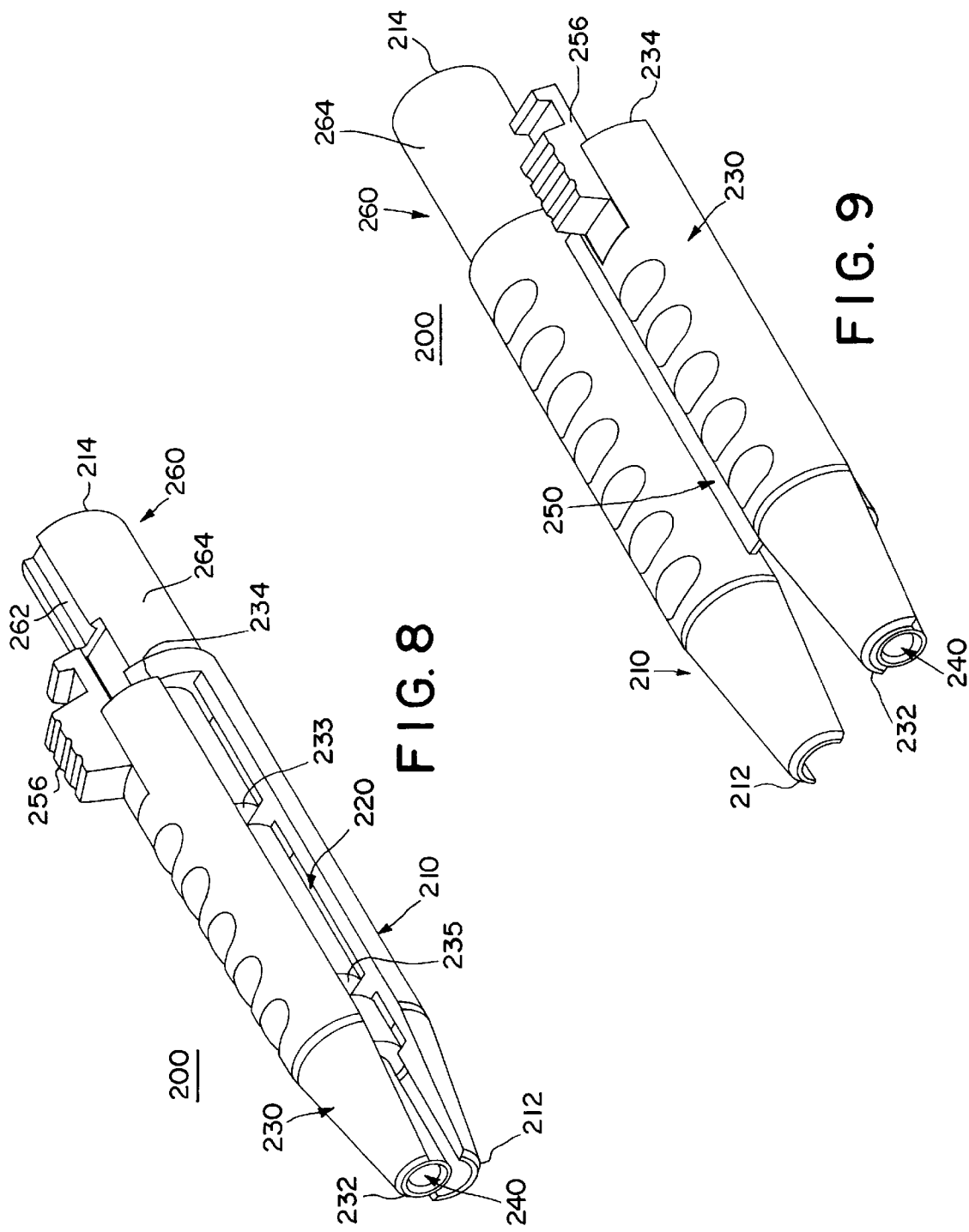

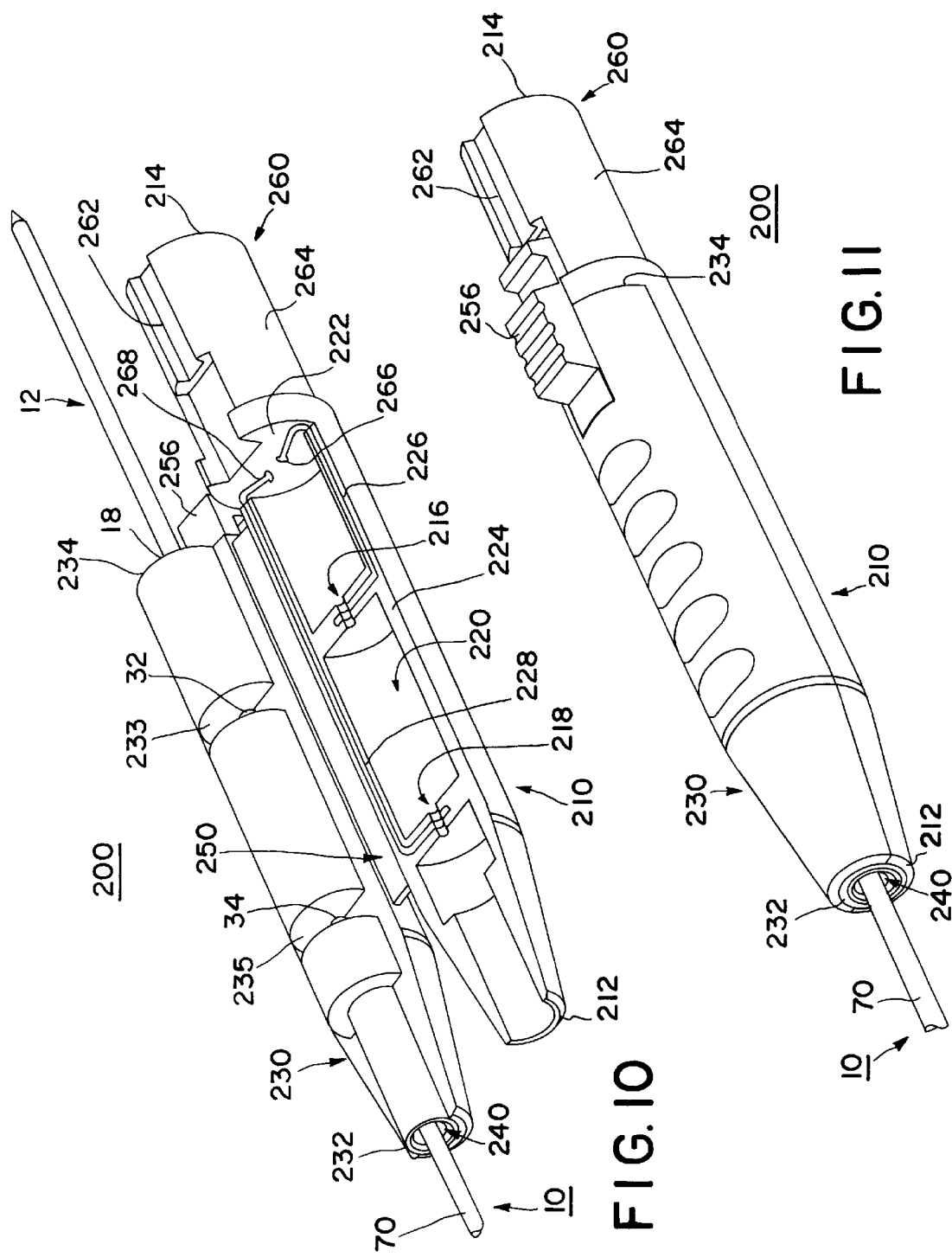

SAFETY ADAPTOR FOR TEMPORARY MEDICAL LEADS

FIELD OF THE INVENTION

The present invention relates generally to adaptors for connecting external medical devices to lead connector elements of medical leads extending percutaneously into a patient's body, and more particularly to adaptors that shield the lead connector elements and connect external medical devices to heart wires for pacing, defibrillating and monitoring the heart and nerve and muscle stimulation wires for stimulating nerves and muscles.

BACKGROUND OF THE INVENTION

Unipolar and bipolar surgically implanted temporary heart wires and temporary leads and nerve, organ, and muscle stimulation leads or wires are well known in the art, some examples of which may be found in the issued U.S. Patents listed in Table I below.

TABLE I

| U.S. Pat. No. | Title |
| --- | --- |
| 3,035,583 | Conductive Sutures |
| 3,125,095 | Flexible Stainless Steel Sutures |
| 3,244,174 | Body Implantable Conductor |
| 3,416,533 | Conductive Catheter |
| 3,664,347 | Electric Heart Stimulation Method and Electrode |
| 3,949,756 | Sutures with Notch Near Needle-Suture Junction |
| 4,010,756 | Heart Pacer Lead Wire with Break-Away Needle |
| B1 4,010,756 | Heart Pacer Lead Wire with Break-Away Needle |
| 4,054,144 | Short-Crimp Surgical Needle |
| 4,338,947 | Positive Fixation Heart Wire |
| 4,341,226 | Temporary Lead with Insertion Tool |
| 4,442,840 | Electrical Connector Apparatus and Method for a Temporary Cardiac Pacing Wire |
| 4,444,207 | Method of Anchoring a Temporary Cardiac Pacing Lead |
| 4,530,368 | Temporary Bipolar Pacing Lead |
| 4,541,440 | Bipolar Epicardial Temporary Pacing Lead |
| 4,553,554 | Electrical Lead and Method for Temporary Cardiac Pacing |
| 4,630,617 | Heart Pacer Lead Wire with Pull-Away Needle |
| 4,633,880 | Surgical Electrode |
| 4,693,258 | Surgical Electrode for Cardiac Pacing and Monitoring |
| 4,972,833 | Epicardial Pacing Lead |
| 5,217,027 | Temporary Cardiac Lead |
| 5,241,957 | Bipolar Temporary Pacing Lead and Connector and Permanent Bipolar Nerve Wire |
| 5,314,463 | Bipolar Nerve Electrode |
| 5,334,045 | Universal Cable Connector for Temporarily Connecting Implantable Leads and Implantable Medical Devices with a Non-Implantable System Analyzer |
| 5,350,419 | Cardiac Pacing Lead |
| 5,423,876 | Intramuscular Lead Having Improved Insertion |
| 5,557,210 | Universal Cable Connector for Temporarily Connecting Implantable Stimulation Leads and Implantable Medical Devices with a Non-Implantable System Analyzer |
| 5,679,022 | Universal Cable Connector for Temporarily Connecting Implantable Stimulation Leads and Implantable Medical Devices with a Non-Implantable System Analyzer |
| 5,782,892 | Medical Lead Adaptor for External Medical Device |
| 5,792,217 | Temporary Bipolar Heart Wire |
| 5,871,528 | Temporary Bipolar Heart Wire |
| 5,931,861 | Medical Lead Adaptor Having Rotatable Locking Clip Mechanism |

All patents listed in Table I are hereby incorporated by reference herein in their respective entireties. As those of ordinary skill in the art will appreciate readily upon reading the Summary of the Invention, Detailed Description of the Preferred Embodiments and Claims set forth below, at least some of the temporary leads and wires disclosed in the patents of Table I may be advantageously employed with the safety adaptor of the present invention.

Certain of the patents listed in Table I disclose surgically implanted temporary heart wires or leads for use with an external unipolar or bipolar cardiac pacemaker and/or monitor or pacing system analyzer (PSA) in a manner that is are well known in the medical field. As described further below, temporary heart wires are implanted in a patient's body to extend between a heart chamber through a percutaneous incision to an external medical device and are removed after a time. Heart wires are sometimes alternatively referred to as temporary pacing leads but are distinguished from endocardial temporary pacing leads that are passed percutaneously through an incision into a vein and transvenously advanced into a heart chamber, typically employing a removable stiffening stylet, as disclosed in the above-referenced, commonly assigned '861 and '892 patents. Such endocardial temporary pacing leads are implanted and used for closed-chest temporary pacing and monitoring of a patient's heart in a variety of single and dual chamber pacing modes. When their use is terminated, they are retracted through the transvenous route, and the incision is closed.

Unipolar heart wires, e.g., the Medtronic® Model 6491, Model 6492, Model 6494, and Model 6500 Temporary Pacing Leads, and bipolar heart wires, e.g., the Medtronic® Model 6495 Temporary Pacing Lead, are shown in the above-referenced, commonly assigned '463, '217 and '328 patents. Such unipolar and bipolar heart wires are implanted in the course of a surgical procedure where the heart is surgically exposed, e.g., to provide post-surgical temporary pacing and monitoring, and are withdrawn through a percutaneous incision by applied traction when their use is to be terminated.

The elongated unipolar and bipolar heart wire bodies are constructed of a single conductor or two conductors, each conductor comprising a number of fine, stainless steel wires twisted together to form a single, flexible, multifilament wire. The major portion of each such conductor within the wire body is typically insulated with a polyethylene, polytetrafluoroethylene, silicone, nylon, or other suitable electrically non-conductive and bio-compatible materials to insulate the wires from one another (in bipolar versions) and from the environment. A short length of each such conductor at the distal end of the heart wire body is exposed to act as a pace/sense electrode when passed into the myocardium. The distal end of the most distal electrode is axially coupled to an elongated retention coil that in turn is coupled axially by a severable, non-conductive, filament to a fine, curved, surgical needle.

The fixation into the myocardium is accomplished with the heart exposed by using the curved needle to pierce the epicardium and to draw the pace/sense electrode(s) and retention coil through a portion of the myocardium without penetrating all the way through the myocardium and into a heart chamber or blood vessel. In this process, the needle is passed back out through the epicardium, and the filament coupling the needle with the fixation coil is severed after electrical testing is completed.

A tubular lead connector element is formed at the proximal end of the heart wire body and electrically connected to each insulated wire in an in-line configuration. A straight, Keith-type, cutting needle extends proximally from the proximal end of the most proximal lead connector element and is used to pierce the thoracic wall to extend the proximal portion of the heart wire body outside the body when the surgical incision accessing the heart is closed. Then, the Keith-type needle is typically clipped or broken off, and each heart wire connector element is coupled to an external medical device.

A similar nerve stimulation wire and procedure of implantation is disclosed in the above-referenced, commonly assigned, '463, '217 and '328 patents.

The proximal connector elements of such temporary endocardial pacing leads and heart wires are typically coupled to terminals of external pacemaker pulse generators, e.g., the Medtronic® Model 5348 and 5388 single chamber or dual chamber pacemaker pulse generators. A direct connection may be made if the lead or wire connector elements are compatible with the external medical device connector terminals and if the lead or wire body is long enough. During surgery, it is necessary to locate the external medical device at a distance and out of the sterile surgical field that exceeds the exposed lead or wire body length. Similarly, it may be necessary to position the external medical device at a distance from a patient who is in post-operative recovery or is otherwise bed-ridden. In these cases, it is necessary to employ elongated cables with cable connector pins that are inserted into female connector terminals of the external medical devices and cable connectors that attach to the exposed heart wire or temporary pacing lead connector elements. Early cable connectors were simply formed as alligator clips that clipped over and made electrical connections with the exposed heart wire or temporary pacing lead connector elements. More recently, cable adaptors of the types disclosed in the above-referenced, commonly assigned, '861, and '892 patents provide enclosures for receiving the connector elements at the proximal ends of the endocardial temporary pacing leads while enabling insertion and removal of stiffening stylets. The above-referenced '463, '217, and '328 adaptors facilitate breaking off the Keith-type needles and attach to the connector elements at the proximal ends of the heart wires or nerve wires.

Concerns relating to the safety of leaving any lead connector element exposed have been voiced by regulatory agencies over many years. It is dangerous to a patient, to conduct electrical current or static electricity through a lead into a patient's body, particularly through a temporary pacing lead or heart wire attached to the heart. Connector regulations IEC 601-1 dictate that medical leads shall be constructed in such a way that no conductive part or surface of a connector element in the part of the medical lead remote from the patient can contact earth or possibly hazardous voltages.

What is needed is an adaptor that meets safety requirements for fully enclosing the lead or wire connector elements while providing simple and reliable electrical and mechanical connections to external medical devices.

SUMMARY OF THE INVENTION

The present invention has certain objects. That is, the present invention provides solutions to problems existing in the prior art. It is an object of the present invention to provide a safe and reliable adaptor for making an electrical connection between external medical device connector terminals and connector elements of a temporary medical lead. Such temporary medical leads include temporary pacing leads and heart wires and muscle, organ, and nerve stimulation leads and wires that extend percutaneously through the skin of a patient. It is a further object of the present invention to provide such a safety adaptor that fully encloses and isolates the medical lead connector elements from the environment and protects from inadvertently conducting an electrical current or charge into the patient's body. Moreover, it is an object of the present invention to provide a simple mechanism for breaking away a beak-away needle attached to the proximal end of the temporary medical lead and then fully enclosing the lead connector elements.

The present invention has certain advantages. More particularly, the safety adaptor of the present invention: (a) is easy to use; (b) attaches to external pacemakers, defibrillators, monitoring equipment, nerve stimulators, and other external medical devices quickly, easily, securely, and reliably; (c) requires no use of an external, separate adaptor or transition box or tool for separating or breaking the needle from the most proximal lead connector element; (d) has few parts; (e) is less expensive to manufacture; (f) helps reduce health care costs; (g) increases patient safety owing to shortened implantation procedure times, lowered risk of accidental electrical injury, and quicker connection to external medical device connector terminals; and (h) satisfies the IEC-1 connector safety regulations.

The safety adaptor of the present invention comprises a first member and a second member. The first member is attached with but movable with respect to the second member and has a elongated bore for receiving a lead proximal end segment including the lead connector elements. Temporary medical leads having a percutaneous penetration needle attached to the lead proximal end are so inserted such that the needle extends out of the elongated bore when the lead connector element(s) are seated within the first member. Preferably, a fulcrum is located at the point where the needle extends from the bore for detaching the break-away needle at a weakened zone connection with the proximal lead connector element, but the needle can be detached by other means. The second member has a breech for receiving the first member and proximal end segment after detachment of the break-away needle. The second member also has a set of breech connector terminals located in the breech for making electrical contact with the lead connector elements upon moving the first member into the breech that are connected via safety adaptor conductors to terminals of an external safety adaptor connector configured to connect with an external medical device connector or a cable.

In use, the break-away needle is advanced through a elongated bore of a first member of the safety adaptor such that the lead connector elements are seated within the elongated bore. Preferably, a weakened zone of the break-away needle is situated against a fulcrum of the first member, and the break-away needle is detached by bending its weakened zone over the fulcrum. The first member of the safety adaptor is moved into the breech of the second member of the safety adaptor such that electrical contact is made between lead connector element(s) and the respective breech connector terminal(s). The external safety adaptor connector terminals that are electrically connected with the breech connector terminals are then coupled with the external medical device connector terminals.

In one preferred embodiment, the safety adaptor comprises an elongated adaptor housing formed of an adaptor body and an adaptor arm that are hinged together at mutually hinged ends thereof and extend to adaptor body and adaptor body free ends, respectively. The hinged ends allow the adaptor arm to be moved from an open position wherein the free end of the adaptor arm is spaced from the adaptor body to a closed position wherein the adaptor arm is received in the breech of the adaptor body and locked therein. The adaptor arm and the breech that receives it in the closed position are shorter in length than the adaptor body, so that the free end of the adaptor arm is not exposed in the closed position. The adaptor arm includes an elongated bore extending from the hinged end to the free end for receiving the lead proximal end segment including the lead connector elements when the adaptor arm is either in the open or closed position. The adaptor body preferably incorporates at least first and second breech electrical terminals that are positioned along the length of the breech to bear against and make electrical contact with the lead connector element or elements inserted into the elongated bore and after the adaptor arm is moved to the closed position.

In a second preferred embodiment, the safety adaptor comprises an elongated adaptor housing formed of an adaptor body that extends between adaptor body first and second ends and has the breech formed therein for receiving an adaptor door. The adaptor door and adaptor body are hinged together at mutually hinged sides of the door and a door frame of the adaptor body. The hinged sides allow the adaptor door to be moved from an open position wherein the adaptor door is spaced from the adaptor body to a closed position wherein the adaptor door is closed against the door frame and the proximal end section of the lead in the elongated bore is received in the breech of the adaptor body and locked therein. The adaptor door and the breech that receives it in the closed position are shorter in length than the adaptor body, so that the second end of the adaptor door is not exposed in the closed position. The adaptor door includes an elongated bore extending from the first end to the second end for receiving the lead proximal end segment including the lead connector elements when the adaptor door is either in the open or closed position. As in the first embodiment, the adaptor body incorporates first and second breech electrical terminals that are positioned along the length of the breech to bear against and make electrical contact with the lead connector element or elements inserted into the elongated bore and after the adaptor door is moved to the closed position.

An exemplary electrical connector is incorporated into both preferred embodiments. The first and second breech electrical terminals are coupled with adaptor connector terminals of a shielded adaptor connector assembly that can be directly connected to a connector terminal assembly of the external medical device or through a separate cable to the connector terminal assembly of the external medical device. The shielded adaptor connector assembly can be formed within the free end of the adaptor body or at the end of a cable extending from the free end of the adaptor body.

A locking mechanism is preferably engaged upon completion of the insertion of the adaptor arm or door into the breech, and the lead connector element or elements bear against and make electrical contact with the adaptor connector terminals. The lead connector element or elements are fully enclosed within the adaptor such that it is not possible to make inadvertent or accidental electrical contact with the lead connector element or elements.

In use with a conventional break-away needle, the break-away needle and the proximal end segment are inserted through the elongated bore so that the break-away needle extends away from the free or second end of the adaptor arm or door. The weakened zone of the break-away needle is at a fulcrum of the free or second end when the lead connector elements are seated in the elongated bore. The break-away needle can be broken away by bending the weakened zone about the fulcrum elements at the free end or otherwise detached. Then, in the first embodiment, the free end of the adaptor arm and the lead connector elements within the elongated bore are pivoted about the hinge and back into the breech. In the second embodiment, the adaptor door is closed on the side hinge into the elongated breech of the adaptor body. Preferably, in both embodiments, a locking mechanism is engaged that prevents re-opening of the adaptor arm or the adaptor door.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIG. 8 is a perspective view of a second embodiment of a safety adaptor of the present invention with the adaptor door in a partially closed position;

FIG. 9 is a perspective view of a second embodiment of FIG. 8 with the adaptor door in an open position;

FIG. 10 is a perspective view of second embodiment of FIG. 8 in the open position with the proximal end segment of the temporary medical lead seated in the elongated bore of the adaptor door and the break-away needle extending from an end thereof; and FIG. 11 is a perspective view of the second embodiment of FIG. 8 with the adaptor door in the closed position and the temporary medical lead connector elements enclosed therein.

DETAILED DESCRIPTION OF THE PREFERRED EMBODIMENTS

Figure 1:
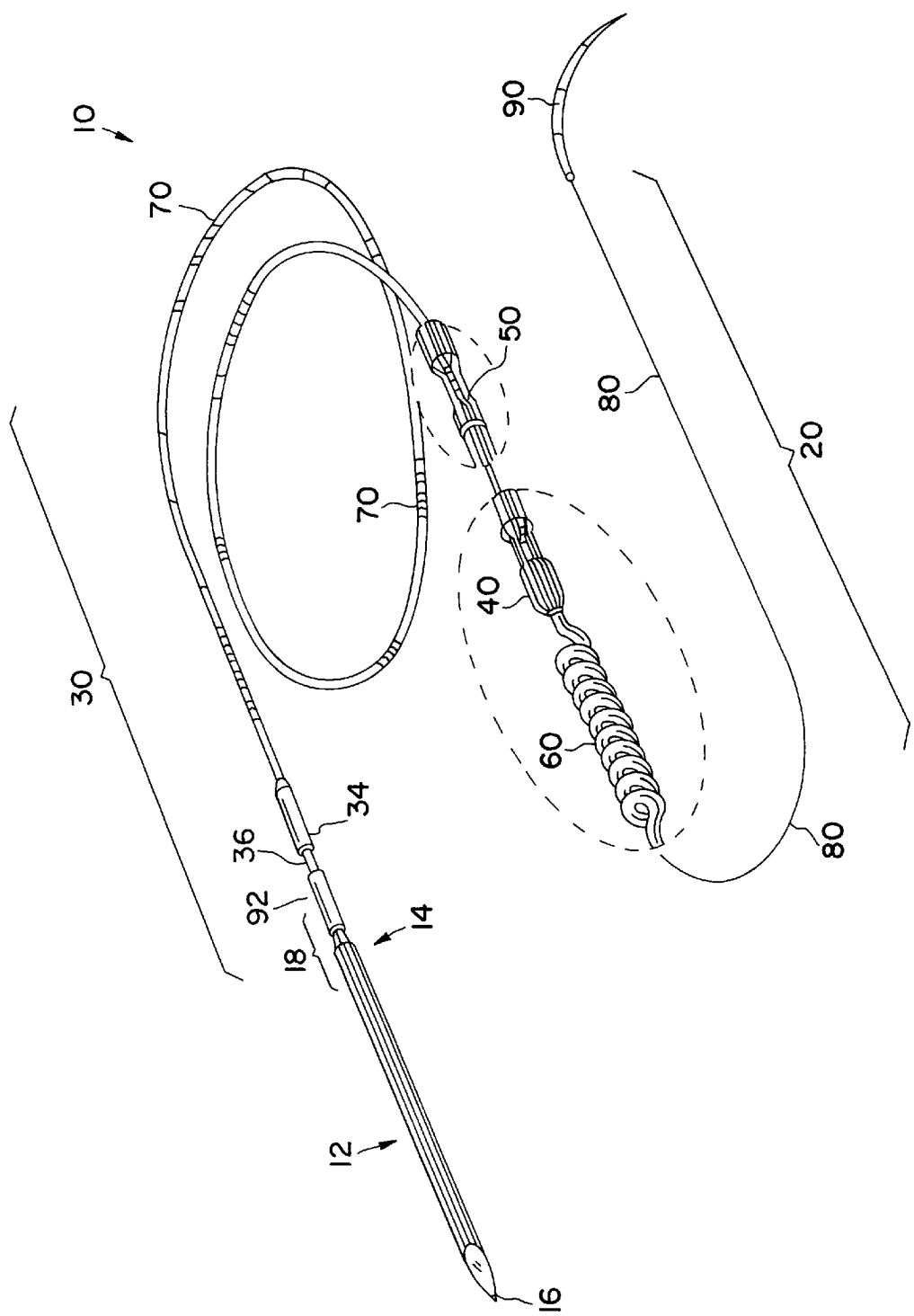
FIG. 1 is a perspective view of a typical bipolar temporary medical lead heart wire that may be advantageously used with the safety adaptor of the present invention in its various embodiments.

The safety adaptor of the present invention may be employed to reliably attach with and fully enclose the connector element(s) located outside a patient's body of a temporary medical lead that extends percutaneously through the patient's skin and to make a secure electrical connection with an external medical device. The temporary medical lead and the external medical device includes those used for nerve, muscle, brain or cardiac stimulation and/or monitoring. In this regard, the following terms have the particular meanings and definitions applicable to the specification and claims as set forth below.

The term "temporary medical lead" and any substantially similar variants thereof means an electrical signal and/or stimulation energy conducting lead that has a proximal end having at least one lead connector element and a break-away needle attached thereto, an elongated lead body, and one or more electrode in a distal end section of the lead body. The electrode(s) is adapted to be implanted at a monitoring and/or stimulation site in a patient's body while the lead body extends through the patient's skin, and the lead connector element is adapted to be indirectly coupled with an external medical device through the safety adaptor of the present invention.

The terms "temporary heart wire", "temporary heart lead" and any substantially similar variants thereof mean a temporary medical lead introduced surgically through the epicardium into the myocardium from the exterior of the heart, where the lead or wire has at least one electrode near its distal end for monitoring, pacing or defibrillating the heart at or near a myocardial or epicardial site, and where the lead or wire has at least one connector element coupled with the break-away needle at its proximal end for electrical connection to an external pacing, monitoring, or defibrillating apparatus. "The terms "heart wire," "heart lead" and any substantially similar variants thereof are synonymous.

The term "proximal" means that portion of an apparatus, or component or element of an apparatus, disposed in closer proximity to the end of the temporary medical lead remaining outside a patient's body following the lead implantation procedure than it is to the distal end of the heart wire implanted in the patient's body.

The term "distal" means that portion of an apparatus, or component or element of an apparatus, disposed in closer proximity to the end of the temporary medical lead that is implanted in the patient's body, e.g., the distal electrodes and retention coil of a heart wire in the myocardium, than it is to the proximal end that remains outside the patient's body following the lead implantation procedure.

For simplicity of illustration, the safety adaptor embodiments of the present invention are disclosed in detail in relation to use with temporary heart wires or nerve stimulation wires having bipolar, in-line connector elements attached to the proximally extending break-away needle. As will be apparent, the safety adaptor embodiments of the present invention can be employed with temporary unipolar or bipolar heart wires or nerve stimulation wires having only a single connector element attached to the proximally extending break-away needle. Similarly, the safety adaptor embodiments of the present invention can be modified to be employed with temporary multi-polar heart wires or nerve, organ or muscle stimulation and monitoring wires having more than two in-line connector elements attached to the proximally extending break-away needle.

FIG. 1 shows a perspective view of an embodiment of a bipolar, in-line, heart wire usable in safety adaptors of the present invention designed specifically for pacing and sensing applications, e.g., the above listed Medtronic® Model 6495 Temporary Pacing Lead. Suitable unipolar and bipolar, heart and nerve, wires are disclosed in greater detail in the above-referenced, commonly assigned '226 and '957 patents, respectively.

Temporary medical lead or wire 10 preferably comprises break-away percutaneous penetrating needle 12, weakened zone 18, a proximal end segment 30 comprising proximal and distal lead connector elements 32 and 34, elongated lead body 70 enclosing first and second conductors, a distal end segment comprising proximal electrode 50, distal electrode 40, retention coil 60, and strand 80, and an a traumatic curved needle 90. It should be noted that the proximal lead connector element 32 may in fact be formed of a distal portion of the break-away needle shaft distal to the weakened zone 18 as shown in the '957 patent. The safety adaptor of the present invention facilitates removal of the break-away needle, encloses the proximal end segment 30, and facilitates connection with an external medical device. However, the safety adaptor is flexible in use, in that it may be employed with an temporary medical lead that does not have a percutaneous penetrating needle or the percutaneous needle may not have a weakened zone, in which case it may be severed by a separate tool as described herein.

Strand 80, preferably formed of polypropylene and constituting a monofilament, forms retention coil 60, attaches to distal electrode 40 and extends to atraumatic curved needle 90. Retention coil 60 ensures secure temporary fixation of the distal electrodes of heart wire 10 in the heart and prevents dislodgment which might otherwise occur were a straight tipped lead employed. Most preferably, one length of polypropylene comprises coil 60 and strand 80. More than one curved needle 90 may be attached to distal end segment 20 of lead 10. For example, the lead body 70 may be bifurcated in distal end segment 20 such that each conductor of lead body 70 terminates in a separate pace/sense electrode, retention coil, and curved needle attached thereto.

Lead body 70 most preferably comprises conductors that provide a high degree of flexibility and superior mechanical and electrical properties. Lead body 70 may comprise any pair of suitable flexible electrical conductors, such as coaxial conductors or so-called "lamp cord" or "zip-cord" (e.g., side-by-side) conductors. Most preferably, lead body 70 is a coaxial pair of inner and outer electrical conductors, where the conductors are formed of helically wound strands of multifilament or twisted stainless steel.

Distal electrodes 40 and 50 are preferably formed of medical grade stainless steel suitable for temporary applications, and are preferably spaced a predetermined distance apart known to optimize the delivery of pacing pulses or the detection and sensing of cardiac electrical signals. Distal electrode 40 is mechanically and electrically connected through the inner conductor (not shown in FIG. 1) to proximal connector element 32 at the proximal end of lead 10, which, in turn, is mechanically connected to blunt end 14 of needle 12 by weakened zone 18. Proximal electrode 50 is mechanically and electrically connected through the outer conductor (not shown in FIG. 1) to distal connector element 34. Distal connector element 34 is located distally along proximal end segment 30 from the proximal connector element 32 and spaced therefrom by insulated inner conductor segment 36.

In-line connector elements 32 and 34 are preferably formed of cylindrically shaped, conductive metal rings that are each electrically connected to a conductor of the lead body 70 and have a circular cross-section and diameter substantially equal to or slightly larger than the diameter of lead body 70. Other structural configurations of connector elements 32 and 34 can be employed with the safety adaptor of the present invention and include, but are not limited to, pin-shaped connectors having rectangular or square cross-sections, reed-shaped connectors, and flexible connectors.

Needle 12, most preferably of the atraumatic type, is a break-away Keith-type needle for piercing the thorax, and has pointed end 16 and blunt end 14. Needle 12 is preferably substantially straight between pointed end 16 and blunt end 14. Pointed end 16 has a cutting edge designed for piercing the thoracic wall of the patient. Preferably, the weakened zone 18 separates the proximal end of proximal connector element 32 from blunt end 14. Or, the proximal connector element 32 may be the part of the break-away needle shaft distal to the weakened zone 18. The weakened zone 18 typically is a narrowed section or a heat treated junction of the needle shaft and the proximal end of the proximal connector element 18.

FIG. 1 shows exemplary features of a temporary medical lead 10 that may be connected with an external medical device through the safety adaptor of the present invention, wherein the temporary medical lead 10 includes at least a break-away needle 12 extending proximally from the proximal lead segment 30 and is intended to be removed after seating the proximal lead segment 30 in a elongated bore of the safety adaptor. Other features of the particular temporary medical lead used with the safety adaptor are not important to the present invention and may take many other forms than those depicted in FIG. 1.

Figure 2:
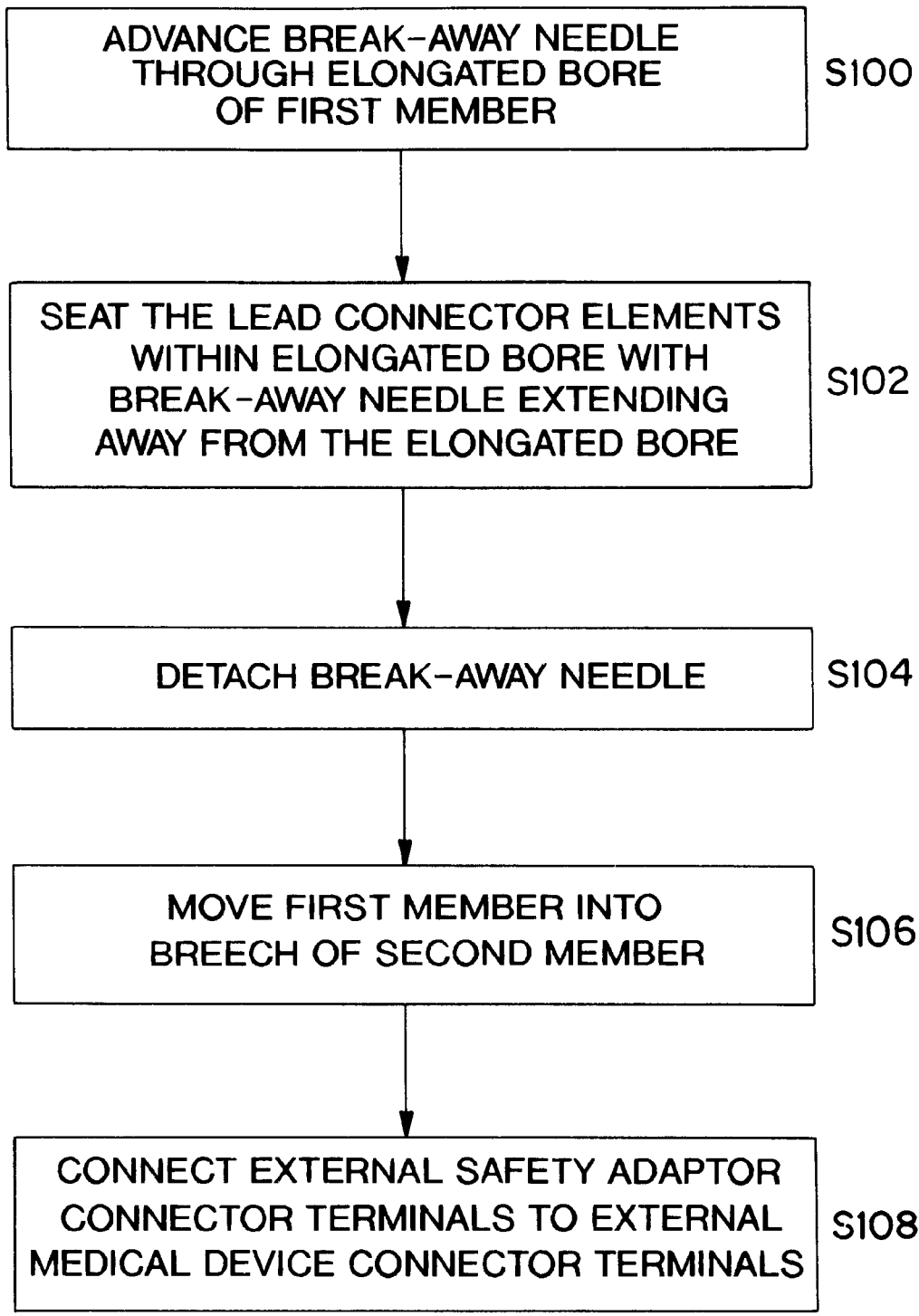
FIG. 2 is a flow chart illustrating the steps of using the safety adaptor of the present invention with an temporary medical lead of the type depicted in FIG. 1.

FIG. 2 depicts how the safety adaptor of the present invention is to be used with the exemplary temporary medical lead of the present invention. In step S100, the temporary medical lead 10 is implanted in the conventional manner in a patient with the break-away needle 12 and at least proximal end segment 30 situated outside the patient's body. The methods of implantation can take any of the forms described in the above-referenced patents for implanting leads of this type, e.g., as is disclosed in the commonly assigned '226, '217, '528, and '463 patents. Generally, after the surgeon draws the distal end segment 20 of lead 10 through the myocardium using curved needle 90, the break-away needle 12 is used as a percutaneous penetration needle to pierce the patient's thorax and it and the proximal lead segment 30 are brought outside the patient's skin.

In steps S100 and S102, the break-away needle 120 is advanced through an elongated bore of a first member of the safety adaptor such that the lead connector elements 32, 34 are seated within the elongated bore and the weakened zone 18 is situated near the end of the elongated bore. As shown in the preferred embodiments, the weakened zone is preferably located between the opposed jaws of a fulcrum at the end of the elongated bore.

In step S104, the break-away needle 120 is detached by bending it over a fulcrum at the end of the elongated bore or by any other suitable means. In step S106, the first member of the safety adaptor is moved into the breech of the second member of the safety adaptor such that electrical contact is made between lead connector elements 32, 34 and respective breech connector terminals. Preferably a locking mechanism is then engaged, and the lead connector elements 32 and 34 are then fully enclosed within the safety adaptor and isolated from electrical ground or potentials. In step S108, the external safety adaptor connector terminals that are electrically connected with the breech connector terminals are then coupled with the external medical device connector terminals either directly or through a compatible cable.

In the first preferred embodiment depicted in FIGS. 3–7, the safety adaptor 100 comprises an elongated adaptor housing formed of an adaptor body 110 and an adaptor arm 130 that are hinged together at mutually hinged ends 112 and 132 thereof. The adaptor body 110 extends away from an adaptor body hinged end 112 to an adaptor body free end 114, and the adaptor arm 130 extends away from a lead receiving adaptor arm hinged end 132 to an adaptor arm free end 134. The lead receiving hinged end 132 and adaptor body hinged end 132 are coupled together by a hinge pin 150 (shown in FIGS. 4 and 5) that allows the adaptor arm 130 to be moved from an open position depicted in FIGS. 3, 4 and 6 to a closed position depicted in FIG. 7.

In the open position, the free end 134 of the adaptor arm 130 is spaced from the adaptor body 110, and in the closed position, the adaptor arm 130 is received in a breech 120 of the adaptor body 110 and locked therein. The adaptor arm 130 and the breech 120 that receives it in the closed position are shorter in length than the adaptor body 110, so that the adaptor body free end 114 is axially aligned with, but is spaced apart from, the adaptor arm free end 134 in the closed position. The breech 120 is also wide enough to accommodates the width of the adaptor arm 130.

Figure 6:
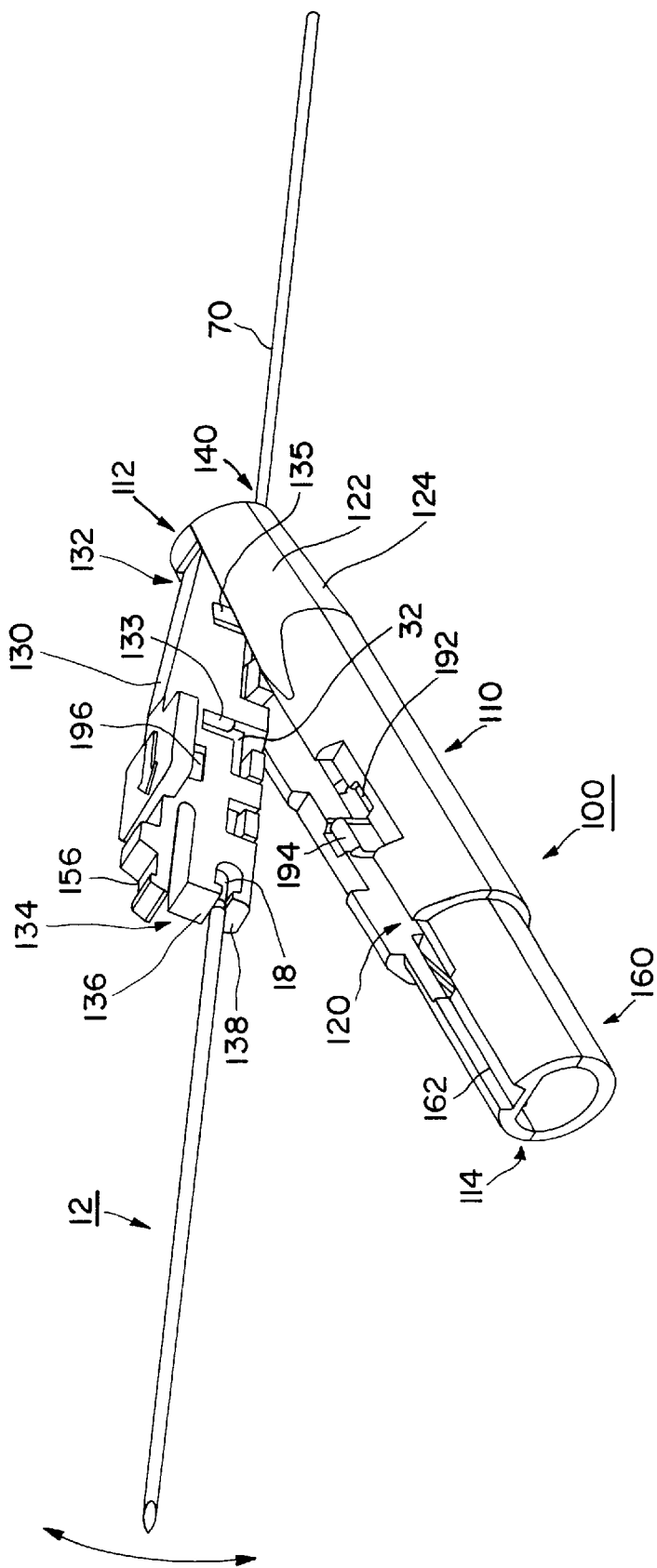
FIG. 6 is a perspective view of the first embodiment of FIG. 3 in the open position with the proximal end segment of the temporary medical lead seated in the elongated bore of the adaptor arm and the break-away needle extending from the free end thereof.
Figure 7:
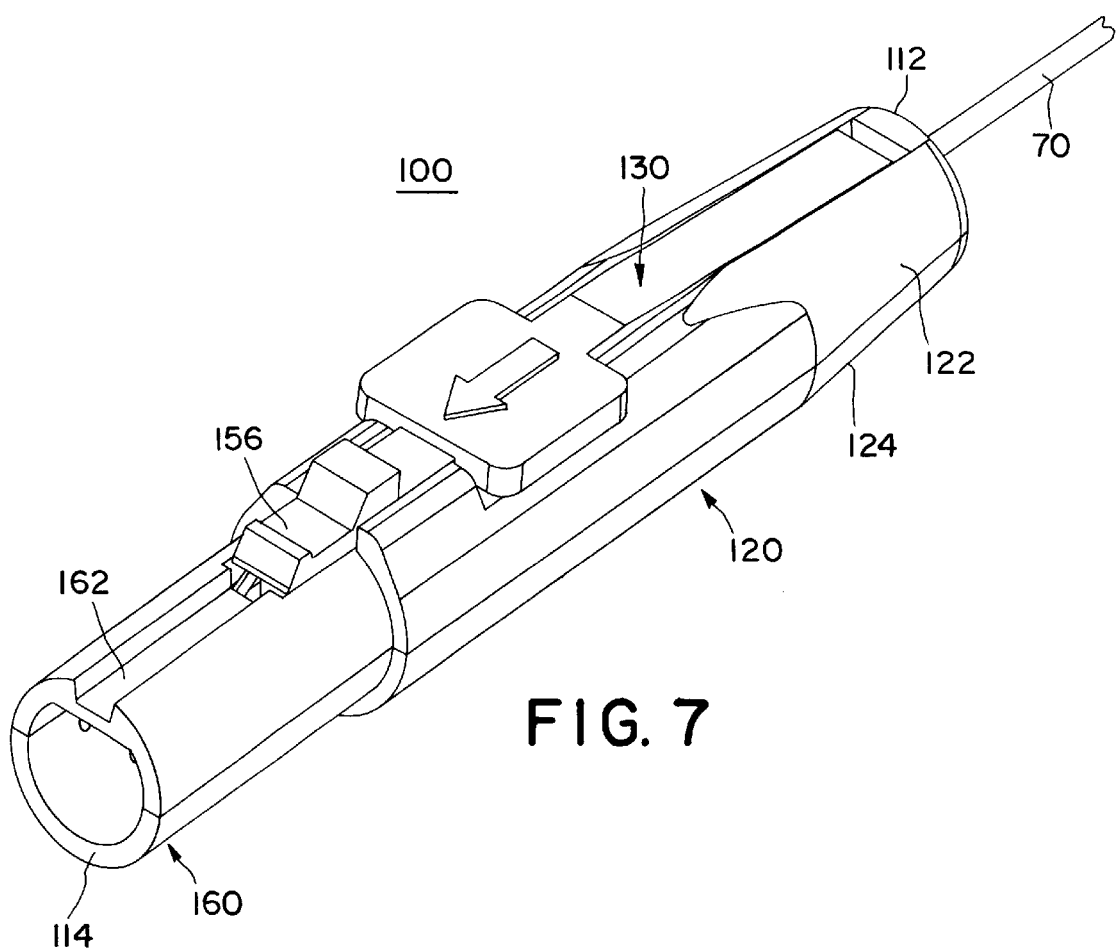
FIG. 7 is a perspective view of the first embodiment of FIG. 3 with the adaptor arm in the closed position and the temporary medical lead connector elements enclosed therein.

The adaptor arm 130 includes an elongated bore 140 extending axially the length of the adaptor arm 130 from the hinged end 132 to the free end 134. The elongated bore 140 is shaped and dimensioned to receive the proximal end segment 30 containing the medical lead connector elements 32 and 34 when the adaptor arm 130 is in the open position as shown in FIG. 6 and in the closed position as shown in FIG. 7. The adaptor arm free end 134 is formed with a set of upper and lower fulcrum jaws or elements 136 and 138 each providing a fulcrum against which the weakened zone 18 can be bent to break off the needle 12 at its blunt end 14. The needle 12 may be clipped off at the point where it exits the elongated bore 140 at the adaptor door free end 134 if the needle does not have a weakened zone 18 or even if it does.

Figure 3:
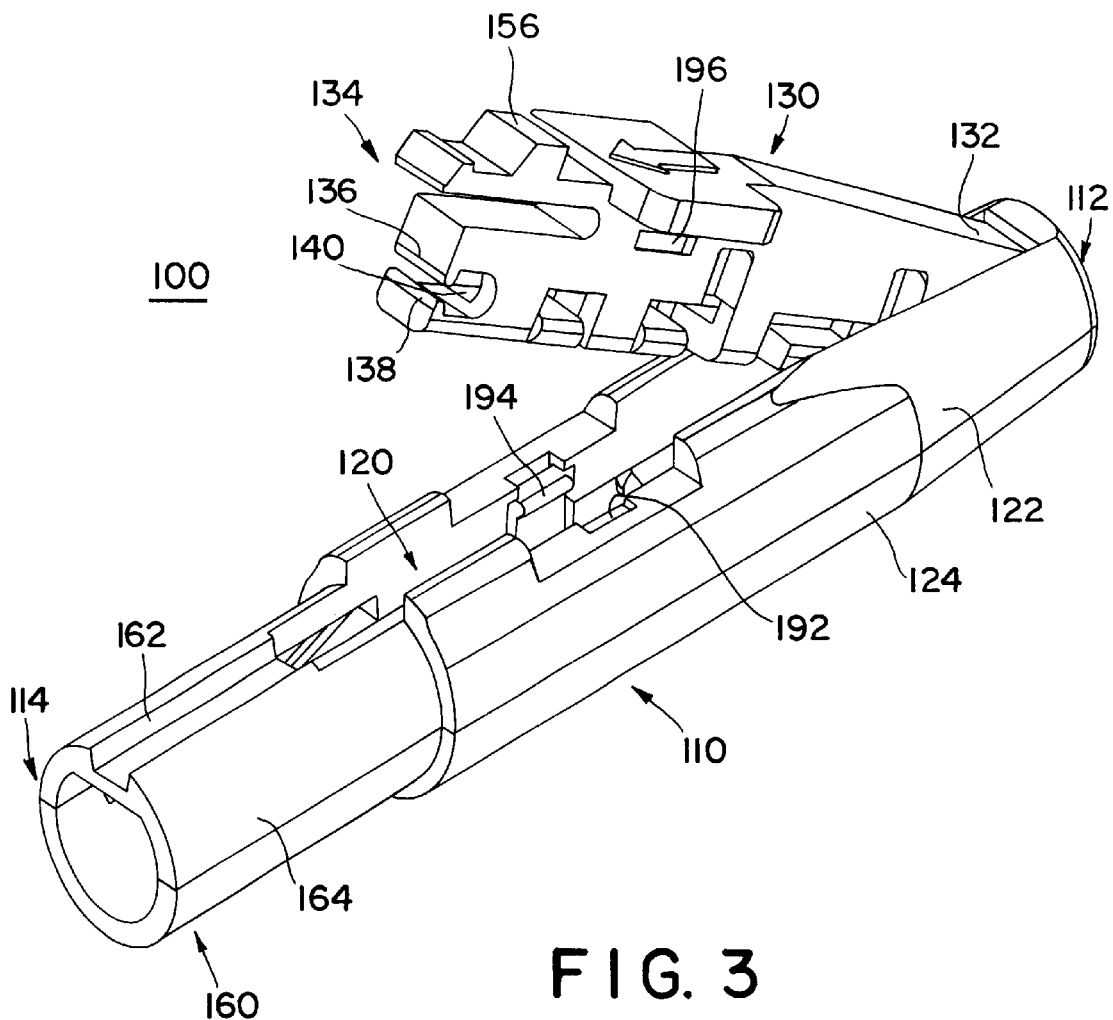
FIG. 3 is a perspective view of a first embodiment of a safety adaptor of the present invention with the adaptor arm in an open position.
Figure 4:
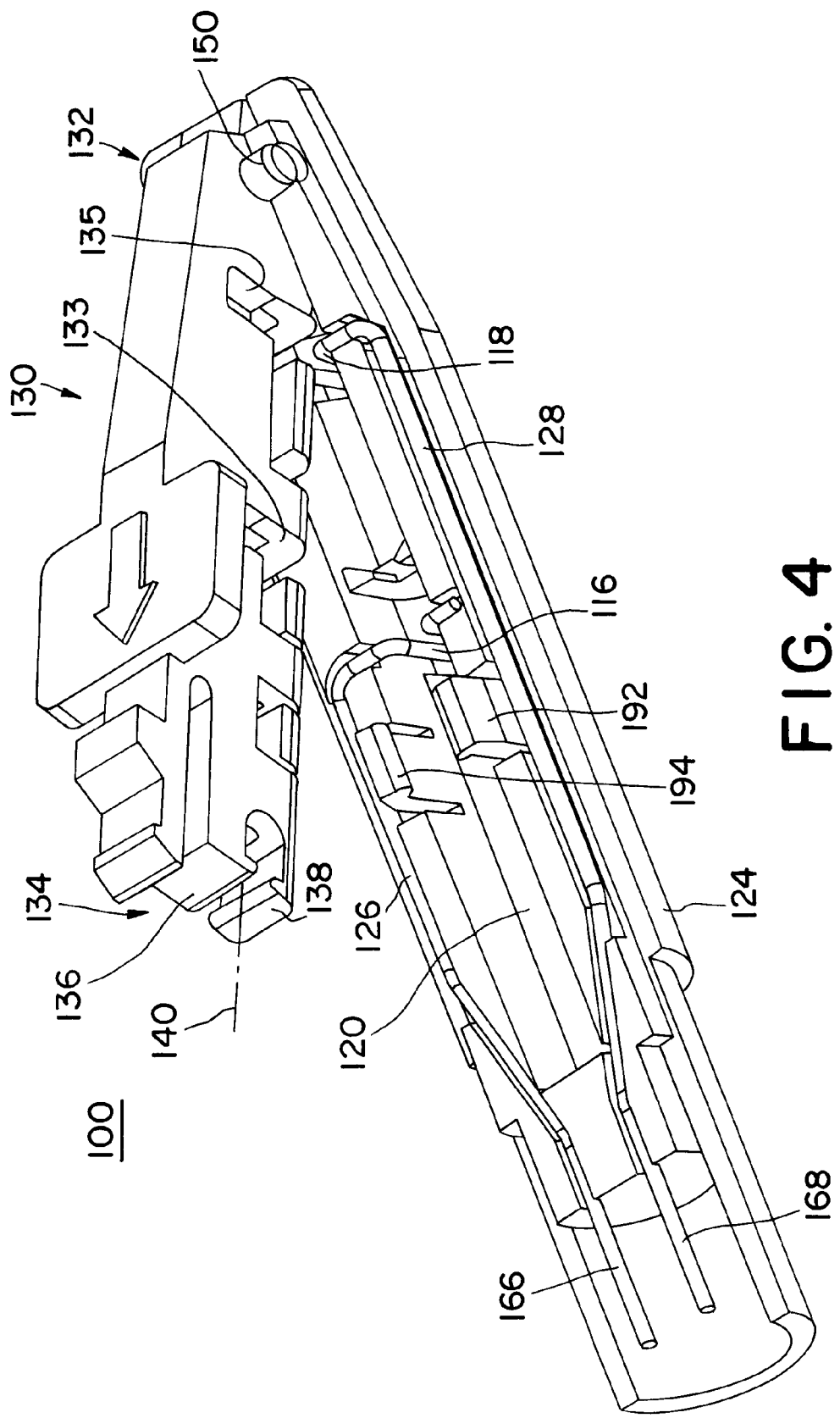
FIG. 4 is a further perspective view of the first embodiment of FIG. 3 in the open position with an adaptor body upper half section removed to view interior components.
Figure 5:
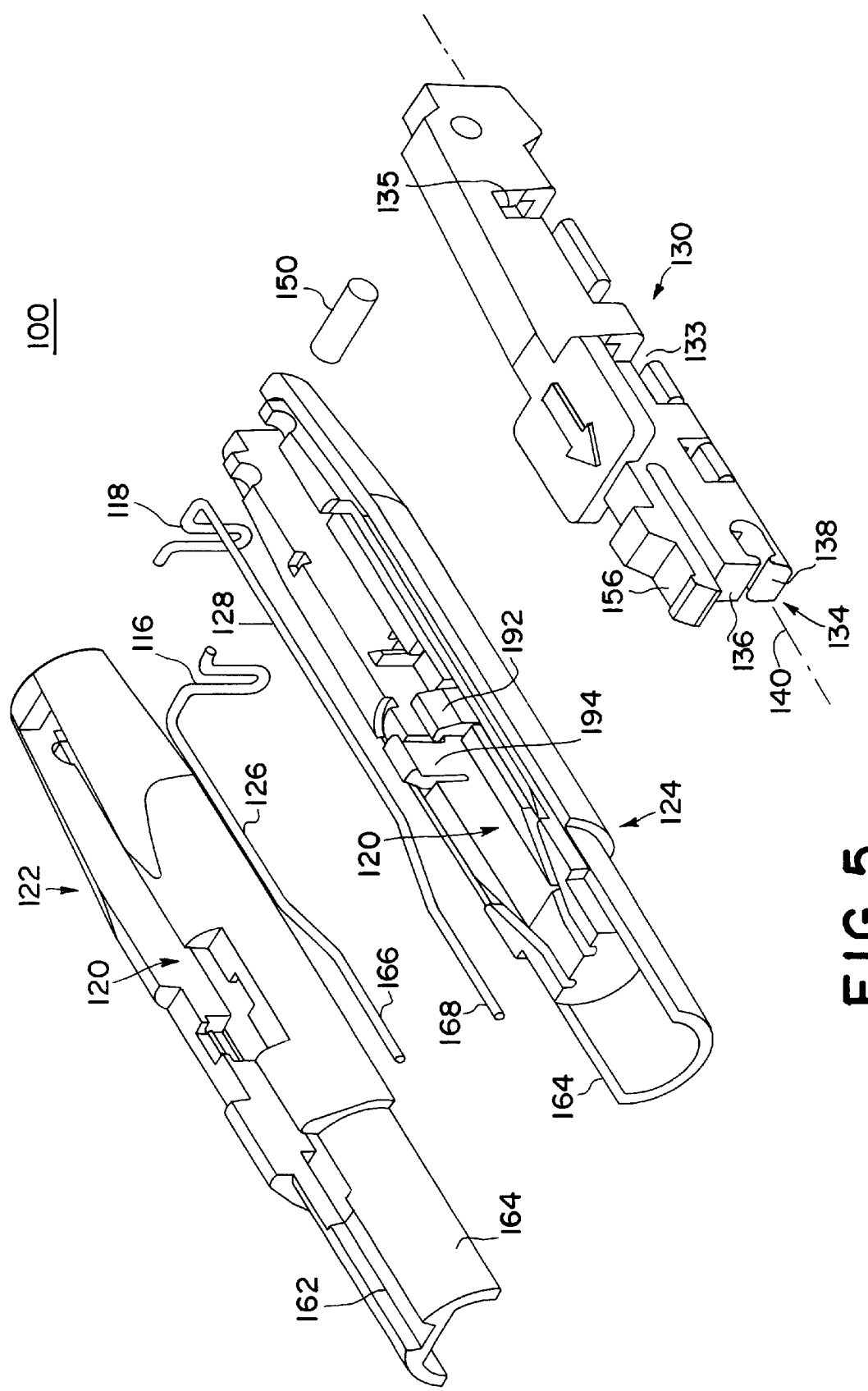
FIG. 5 is an exploded perspective view of the components of the first embodiment of FIG. 3.

The adaptor body 110 is formed of an upper body half section 122 and a lower body half section 124 (shown separated in FIG. 5) that are assembled together as shown in FIG. 3. The adaptor body 110 incorporates first and second breech electrical terminals 116 and 118 that are positioned along the length of the breech 120 as shown in FIGS. 4 and 5 to bear against and make electrical contact with the lead connector elements 32 and 34 inserted into the elongated bore 140.

A locking mechanism is preferably provided for locking the safety adaptor arm 130 in the closed position shown in FIG. 7. A pair of living hinge latches 192 and 194 formed in lower half section 124 (FIG. 5) project upward along each side of the side walls of the breech 120 and engage with a like pair of catches formed in the side walls of the adaptor arm 130 to operate as a locking mechanism. Only the adaptor arm catch 196 is visible (FIGS. 3 and 6) that engages with latch 192. The adaptor arm 130 enclosing the lead proximal end segment cannot be removed from the breech once the locking mechanism is engaged.

The first and second breech electrical terminals 116 and 118 are coupled through adaptor conductors 126 and 128, respectively, with adaptor connector pins 166 and 168, respectively of a shielded, external adaptor connector 160 that can be directly connected to a connector terminal assembly of the external medical device (not shown). As shown in FIG. 5, the first and second breech electrical terminals 116 and 118, the adaptor conductors 126 and 128 and the adaptor connector pins 166 and 168 can be formed of two relatively stiff conductor wires that are fitted into channels of the upper and lower adaptor body sections 122 and 124. The breech electrical terminals 116 and 118 are formed in a U-shape and the side walls of the lead connector elements 32 and 34 are nested tightly into and against the U-shaped breech electrical terminals 116 and 118. The adaptor arm 130 is formed with cut-out sections 133 and 135 along the elongated bore 140 that expose about three-fourths of the circumference of the lead connector elements 32 and 34 to be nested within the U-shaped breech electrical terminals 116 and 118.

The external adaptor connector assembly 160 is formed of the adaptor body free end 114 and comprises the non-conductive cylindrical shield 164 surrounding the adaptor connector pins 166 and 168 and having a keyway 162 formed in the upper surface of upper body half section 122. In addition, the adaptor arm free end 134 is shaped to provide a living hinge latch 156 which is aligned with the keyway 162 when the adaptor arm 130 is depressed into the breech 120. The latch 156 is adapted to engage a catch of the connector assembly of the implantable medical device (not shown) when the external adaptor connector is attached to it. The size, shape and positions of the shield 164, keyway 162 and adaptor connector pins 166 and 168 are selected to conform with a standardized, two pin, male connector, sometimes referred to as a "Hypertronics" connector. The external medical device is provided with a female connector (not shown) that mates with these physical features of the external adaptor connector 160. The latch 156 and the mating catch thus secures the connection and also helps keep the adaptor arm 130 in the breech 120. The external adaptor connector 160 can also be formed at the end of a cable coupled to the adaptor conductors 126 and 128 at the adaptor body free end 114. Or, a separate cable may be provided with a female connector that connects with the external adaptor connector 160 and extends to the external medical device where it is either permanently attached or connects through a further set of mating connectors with the external medical device.

The attachment of the safety adaptor 100 to the conventional temporary medical lead 10 in accordance with steps S100–S106 is illustrated in FIGS. 6 and 7. In FIG. 6, the break-away needle 12 has been inserted in the direction of the arrow formed in the upper surface of adaptor arm 130 into a bore opening at the adaptor arm hinged end 132 and advanced through the elongated bore 140 so that the break-away needle extends away from the adaptor arm free end 134. The weakened zone 18 of the break-away needle 12 is located at the free end 134, and the lead connector elements 32 and 34 are seated in the elongated bore 140 and exposed by the cut-out sections 133 and 135, respectively. The break-away needle 12 can be broken away in step S104 by bending the weakened zone 18 about the upper and/or lower fulcrum jaws or elements 136 and 138. Or the detachment of the break-away needle 12 may be accomplished by clipping it off. The assembly of the lead proximal end segment 30 within the elongated bore 140 and the adaptor arm 130 is then able to be rotated about hinge 150 and moved into the breech 120 in step S106. Preferably, the safety adaptor 100 is locked onto the proximal end segment 30 by the locking mechanism so that the safety adaptor 100 can be handled or set aside pending completion of other surgical procedures without any danger that the lead connector elements 32 and 34 become exposed.

In the second preferred embodiment depicted in FIGS. 8–11, the safety adaptor 200 comprises an elongated adaptor housing formed of an adaptor body 210 and an adaptor door 230 that are hinged together along a side thereof by a living hinge 250. The adaptor body 210 extends between a first adaptor body end 212 and a second adaptor body end 214 that is configured with an external adaptor connector assembly 260. The adaptor door 230 normally extends outward from the side that hinge 250 is attached to as shown in FIGS. 9 and 10 by virtue of the hinge stiffness. The adaptor door 230 has a length between the door first end and the door second end dictated by the length of the elongated bore 240 required to receive the proximal end segment 30 in a unipolar or bipolar or multi-polar configuration. A lead insertion opening to the elongated bore 240 is formed in the adaptor door first end 232, and a needle exiting opening from the elongated bore 240 is formed in the adaptor door second end 234. The side hinge 250 allows the adaptor door 230 to be moved from an open position depicted in FIGS. 9 and 10 to a partly closed position and a fully closed position depicted in FIGS. 8 and 11, respectively.

In the closed position, the adaptor door 230 bears against the frame surface 224 of the adaptor body 210 and its inwardly projecting structure for enclosing the elongated bore 240 is received in a breech 220 of the adaptor body 210 that is shaped in a complementary manner to the inwardly projecting structure of the adaptor door 230. The adaptor door 230 is locked against the frame surface (for simplicity, a locking mechanism apart from latch 256 is not depicted in the figures). The adaptor door 230 and the breech 220 that receives it in the closed position are shorter in length than the adaptor body 210, so that the adaptor body second end 214 is axially aligned with, but is spaced apart from, the adaptor door second end 234 in the closed position. The breech 220 is also shaped to accommodates the interior shape of the adaptor door 230 as shown in FIG. 10.

The adaptor door 230 includes the elongated bore 240 extending axially the length of the adaptor door 230 between the adaptor door first and second ends 232 and 234. The elongated bore 240 is flared outward in diameter at the adaptor door first end 232 and then diminishes in diameter such that it is shaped and dimensioned to receive the proximal end segment 30 containing the medical lead connector elements 32 and 34 when the adaptor door 230 is in the open position as shown in FIG. 10 and in the closed position as shown in FIG. 11. The adaptor door second end 234 may be formed with a fulcrum element of a type similar to upper and lower fulcrum jaws or elements 136 and 138 described above to provide a fulcrum against which the weakened zone 18 can be bent to break off the break-away needle 12 at its blunt end 14. The needle 12 may be clipped off at the point where it exits the elongated bore 240 at the adaptor door second end 234 if the needle does or does not have a weakened zone 18.

The adaptor body 210 incorporates first and second breech electrical terminals 216 and 218 that are positioned along the length of the breech 220 as shown in FIGS. 4 and 5 to bear against and make electrical contact with the lead connector elements 32 and 34 inserted into the elongated bore 240. The first and second breech electrical terminals 216 and 218 are coupled through adaptor conductors 226 and 228, respectively, with adaptor connector pins 266 and 268, respectively of a shielded, external adaptor connector 260 that can be directly connected to a connector terminal assembly of the external medical device (not shown). As shown in FIG. 5, the first and second breech electrical terminals 216 and 218, the adaptor conductors 226 and 228 and the adaptor connector pins 266 and 268 can be formed of two relatively stiff conductor wires that are molded into channels of the surface 224 of the adaptor body 210 and extend through the end wall 222 of the breech 220. The breech electrical terminals 216 and 218 are formed in a U-shape and the side walls of the lead connector elements 32 and 34 are nested tightly into and against the U-shaped breech electrical terminals 216 and 218. The adaptor door 230 is formed with cut-out sections 233 and 235 along the elongated bore 240 that expose about three-fourths of the circumference of the lead connector elements 32 and 34 to be nested within the U-shaped breech electrical terminals 216 and 218.

The external adaptor connector assembly 260 is formed of the adaptor body free end 214 and comprises the non-conductive cylindrical shield 264 surrounding a pair of adaptor connector pins 266 and 268 extending through breech end wall 222 and having a keyway 262 formed in the upper surface of non-conductive cylindrical shield 264. In addition, the adaptor door second end 234 is shaped to provide a living hinge latch 256 which is aligned with the keyway 262 when the adaptor door 230 is depressed into the breech 220. The latch 256 is adapted to engage a catch of the connector assembly of the implantable medical device (not shown) when the external adaptor connector is attached to it. The size, shape and positions of the shield 264, keyway 262 and adaptor connector pins 266 and 268 are selected to conform with a standardized, two pin, male connector. The external medical device is provided with a female connector (not shown) that mates with these physical features of the external adaptor connector 260. The latch 256 and the mating catch thus secures the connection and also helps keep the adaptor arm 230 in the breech 220. The external adaptor connector 260 can also be formed at the end of a cable coupled to the adaptor conductors 226 and 228 at the adaptor body free end 214.

The attachment of the safety adaptor 200 to the conventional temporary medical lead 10 in accordance with steps S100–S106 is illustrated in FIGS. 10 and 11. In FIG. 10, the break-away needle 12 has been inserted into a bore opening of the elongated bore 240 at the adaptor door first end 232 and advanced through the elongated bore 240 so that the break-away needle 12 extends away from the adaptor door second end 234. The weakened zone 18 of the break-away needle 12 is located at the second end 234, and the lead connector elements 32 and 34 are seated in the elongated bore 240 and exposed through the cut-out sections 233 and 235, respectively. The break-away needle 12 can be broken away in step S104 by bending the weakened zone 18 about the fulcrum formed at the second end 234 or by clipping it off with a separate clipping tool. The assembly of the lead proximal end segment 30 within the elongated bore 240 and the adaptor door 230 is then able to be pivoted about hinge 250 and moved into the breech 220 in step S106. Preferably, the safety adaptor 200 is locked onto the proximal end segment 30 by a locking mechanism similar to locking mechanism 192–196 of the first embodiment so that the safety adaptor 200 can be handled or set aside pending completion of other surgical procedures without any danger that the lead connector elements 32 and 34 become exposed. Or the locking may be accomplished by the insertion of the external connector assembly 260 into a mating connector of the external medical device or a further cable that extends to the external medical device as described above.

The present invention permits reliable and secure electrical connections to be established securely, reliably, quickly and safely between at least two electrodes and the external electrical medical devices. Thus, the present invention may simplify implant procedures, reduce the amount of time required to complete such procedures, and increase the reliability and safety of the heart wire system respecting prior art heart wire systems.

All patents listed hereinabove are hereby incorporated by reference into the specification hereof in their respective entireties. As those of ordinary skill in the art will appreciate readily upon reading the Summary of the Invention, Detailed Description of the Preferred Embodiments and Claims set forth herein, at least some of the devices and methods disclosed in those patents may be modified advantageously in accordance with the teachings of the present invention.

While the present invention has been illustrated and described with particularity in terms of a preferred embodiment, it should be understood that no limitation of the scope of the invention is intended thereby. It should also be understood that many equivalents to the particular embodiments described herein incorporating the principles of the present invention will occur to those of ordinary skill in the art and yet be within the scope of the appended claims. The scope of the invention is defined only by the claims appended hereto. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A safety adaptor for connecting an external medical device to at least one lead connector element of a medical lead extending percutaneously into a patient's body, comprising:

an elongated first member having an elongated bore extending between a first member first end and a first member second end for receiving a lead proximal end segment including the lead connector element upon insertion of the lead proximal end segment therein through the first member first end;

a second member having a breech for receiving the first member and the proximal end segment, the second member having at least one breech connector terminal located in the breech for making electrical contact with the at least one lead connector element within the elongated bore upon moving the first member into the breech; and a hinge coupled between the first member and the second member to enable movement of the first member with respect to the second member between an open position wherein the lead proximal end is insertable into the elongated bore of the first member and a closed position wherein the at least one connector element is brought into contact with the at least one breech connector terminal such that the at least one connector element is electrically isolated within the safety adaptor.

2. The safety adaptor of claim 1, wherein the first member has an first member length between the first member first end and second end, the second member has an second member length between the second member first end and the second member second end, and the breech has a breech length shorter than the second member length and sufficient to receive the first member length in the closed position such that the second end of the first member is not exposed in the closed position.

3. The safety adaptor of claim 1 particularly adapted for connecting an external medical device to at least one lead connector element of a medical lead extending percutaneously into a patient's body and having a percutaneous penetration needle attached to the lead proximal end, wherein:

the elongated bore extends through a needle exiting opening of the first member second end, such that the percutaneous penetration needle is extended through the needle exiting opening upon insertion of the lead proximal end segment into the elongated bore to enable removal of the percutaneous needle.

4. The safety adaptor of claim 1 particularly adapted for connecting an external medical device to at least one lead connector element of a medical lead extending percutaneously into a patient's body and having a percutaneous penetration needle with a weakened zone attached to the lead proximal end, wherein:
   a fulcrum is formed at the first member second end; and
   the elongated bore extends through a needle exiting opening of the first member second end, such that the percutaneous penetration needle is extended through the needle exiting opening and the weakened zone is positioned in working relation with the fulcrum upon insertion of the lead proximal end segment into the elongated bore to enable removal of the percutaneous needle by use of the fulcrum.

5. The safety adaptor of claim 1, wherein the second member further comprises:
   an external safety adaptor connector located at the second member second end configured to connect with an external medical device connector or a cable; and
   a safety adaptor conductor extending between the external safety adaptor connector and the breech electrical terminal.

6. The safety adaptor of claim 5, further comprising a lock mechanism that engages upon connection of the external safety adaptor connector located at the second member second end with an external medical device connector or a cable to prevent the movement of the first member from the closed position.

7. The safety adaptor of claim 1, further comprising a lock mechanism that engages upon movement of the first member into the closed position to prevent the movement of the first member from the closed position.

8. The safety adaptor of claim 1, wherein;
   the first member is formed with at least one cut-out section along the elongated bore that exposes a portion of the circumference of the at least one lead connector element of the proximal end section of the lead disposed in the elongated bore; and
   the at least one breech electrical terminal is formed in a shape and located to engage the exposed portion of the circumference of the at least one lead connector element of the proximal end section of the lead disposed in the elongated bore when the first member is moved into the breech.

9. The safety adaptor of claim 1, wherein:
   the first member comprises an elongated adaptor arm, the first member first end is an adaptor arm free end, the first member second end is a an adaptor arm hinged end, and the elongated bore extends between a lead insertion bore end formed in the adaptor arm hinged end and the adaptor arm free end;
   the second member comprises an elongated adaptor body, the second member first end is an adaptor body free end, and the second member second end is a an adaptor body hinged end; and
   a hinge connects the adaptor body hinged end and the adaptor arm hinged end to enable movement of the adaptor arm from the open position to the closed position such that the elongated adaptor arm is fitted into the breech of the adaptor body.

10. The safety adaptor of claim 9, wherein the adaptor arm has an adaptor arm length between the adaptor arm hinged end and free end, the adaptor body has an adaptor body length between the adaptor body hinged end and the adaptor body free end, and the breech has a breech length shorter than the adaptor body length and sufficient to receive the adaptor arm length in the closed position such that the free end of the adaptor arm is not exposed in the closed position.

11. The safety adaptor of claim 9, further comprising a lock mechanism that engages upon movement of the adaptor arm into the closed position to prevent the movement of the adaptor arm from the closed position.

12. The safety adaptor of claim 9 particularly adapted for connecting an external medical device to at least one lead connector element of a medical lead extending percutaneously into a patient's body and having a percutaneous penetration needle attached to the lead proximal end, wherein:
   the elongated bore extends through a needle exiting opening of the adaptor arm free end, such that the percutaneous penetration needle is extended through the needle exiting opening upon insertion of the lead proximal end segment into the elongated bore to enable removal of the percutaneous needle.

13. The safety adaptor of claim 9 particularly adapted for connecting an external medical device to at least one lead connector element of a medical lead extending percutaneously into a patient's body and having a percutaneous penetration needle with a weakened zone attached to the lead proximal end, wherein:
   a fulcrum is formed at the adaptor arm free end; and
   the elongated bore extends through a needle exiting opening of the adaptor arm free end, such that the percutaneous penetration needle is extended through the needle exiting opening and the weakened zone is positioned in working relation with the fulcrum upon insertion of the lead proximal end segment into the elongated bore to enable removal of the percutaneous needle by use of the fulcrum.

14. The safety adaptor of claim 9, wherein the adaptor body further comprises:
   an external safety adaptor connector located at the adaptor body free end configured to connect with an external medical device connector or a cable; and
   a safety adaptor conductor extending between the external safety adaptor connector and the breech electrical terminal.

15. The safety adaptor of claim 14, further comprising a lock mechanism that engages upon connection of the external safety adaptor connector located at the adaptor body free end with an external medical device connector or a cable to prevent the movement of the adaptor arm from the closed position.

16. The safety adaptor of claim 9, wherein;
   the adaptor arm is formed with at least one cut-out section along the elongated bore that exposes a portion of the circumference of the at least one lead connector element of the proximal end section of the lead disposed in the elongated bore; and
   the at least one breech electrical terminal is formed in a U-shape and located to engage the exposed portion of the circumference of the at least one lead connector element of the proximal end section of the lead disposed in the elongated bore when the adaptor arm is moved into the breech.

17. The safety adaptor of claim 1, wherein:
   the first member comprises an elongated adaptor door having door sides extending between adaptor door first and second ends;

the second member comprises an elongated adaptor body having a door frame surface against which the adaptor door closes in the closed position; and a hinge extends between the adaptor body door frame and an adaptor door side to enable movement of the adaptor door from the open position to the closed position, such that the elongated adaptor door is fitted into the breech of the adaptor body and against the door frame surface.

18. The safety adaptor of claim 17, wherein the adaptor door has an adaptor door length between the adaptor door first end and second end, the adaptor body has an adaptor body length between the adaptor body first end and the adaptor body second end, and the breech has a breech length shorter than the adaptor body length and sufficient to receive the adaptor door length in the closed position such that the second end of the adaptor door is not exposed in the closed position.

19. The safety adaptor of claim 17 particularly adapted for connecting an external medical device to at least one lead connector element of a medical lead extending percutaneously into a patient's body and having a percutaneous penetration needle attached to the lead proximal end, wherein:

the elongated bore extends through a needle exiting opening of the adaptor door second end, such that the percutaneous penetration needle is extended through the needle exiting opening upon insertion of the lead proximal end segment into the elongated bore to enable removal of the percutaneous needle.

20. The safety adaptor of claim 17, further comprising a lock mechanism that engages upon movement of the adaptor door into the closed position to prevent the movement of the adaptor door from the closed position.

21. The safety adaptor of claim 17 particularly adapted for connecting an external medical device to at least one lead connector element of a medical lead extending percutaneously into a patient's body and having a percutaneous penetration needle with a weakened zone attached to the lead proximal end, wherein:

a fulcrum is formed at the adaptor door second end; and the elongated bore extends through a needle exiting opening of the adaptor door second end, such that the percutaneous penetration needle is extended through the needle exiting opening and the weakened zone is positioned in working relation with the fulcrum upon insertion of the lead proximal end segment into the elongated bore to enable removal of the percutaneous needle by use of the fulcrum.

22. The safety adaptor of claim 17, wherein the adaptor body further comprises:

an external safety adaptor connector located at the adaptor body second end configured to connect with an external medical device connector or a cable; and a safety adaptor conductor extending between the external safety adaptor connector and the breech electrical terminal.

23. The safety adaptor of claim 22, further comprising a lock mechanism that engages upon connection of the external safety adaptor connector located at the adaptor body second end with an external medical device connector or a cable to prevent the movement of the adaptor door from the closed position.

24. The safety adaptor of claim 17, wherein;

the adaptor door is formed with at least one cut-out section along the elongated bore that exposes a portion of the circumference of the at least one lead connector element of the proximal end section of the lead disposed in the elongated bore; and the at least one breech electrical terminal is formed in a U-shape and located to engage the exposed portion of the circumference of the at least one lead connector element of the proximal end section of the lead disposed in the elongated bore when the adaptor door is moved into the breech.

25. A method of using a safety adaptor having a first member and a second member for connecting an external medical device to at least one lead connector element of a medical lead extending percutaneously into a patient's body wherein a hinge between the first member and the second member enables movement of the first member with respect to the second member between an open position enabling the insertion of the lead proximal end into an elongated bore of the first member and a closed position enabling contact between the at least one connector element and at least one breech connector terminal, comprising:

inserting a lead proximal end segment including the lead connector element into the elongated bore of the first member, the elongated bore extending between a first member first end and a first member second end;

moving the first member into a breech of the second member that receives the first member and the proximal end segment;

making electrical contact between the at least one lead connector element within the elongated bore and the at least one breech connector terminal located in the breech upon moving the first member into the breach of the second member, such that the at least one connector element is electrically isolated within the safety adaptor; and electrically coupling the safety adaptor to the external medical device.

26. The method of claim 25, wherein the first member has an first member length between the first member first end and second end, the second member has an second member length between the second member first end and the second member second end, and the breech has a breech length shorter than the second member length and sufficient to receive the first member length in the closed position such that the second end of the first member is not exposed in the closed position.

27. The method of claim 25 particularly adapted for connecting an external medical device to at least one lead connector element of a medical lead extending percutaneously into a patient's body and having a percutaneous penetration needle attached to the lead proximal end, wherein:

the elongated bore extends through a needle exiting opening of the first member second end, and the inserting step further comprises:

extending the percutaneous penetration needle through the needle exiting opening upon insertion of the lead proximal end segment into the elongated bore to enable removal of the percutaneous needle; and removing the percutaneous penetration needle.

28. The method of claim 25 particularly adapted for connecting an external medical device to at least one lead connector element of a medical lead extending percutaneously into a patient's body and having a percutaneous penetration needle with a weakened zone attached to the lead proximal end, wherein:

a fulcrum is formed at the first member second end; and the elongated bore extends through a needle exiting opening of the first member second end; and the inserting step further comprises:
   extending the percutaneous penetration needle through the needle exiting opening upon insertion of the lead proximal end segment into the elongated bore such that the weakened zone is positioned in working relation with the fulcrum to enable removal of the percutaneous needle; and
   removing the percutaneous penetration needle by bending the weakened zone against the fulcrum until the weakened zone breaks.

29. The method of claim 25, wherein the second member further comprises:
   an external safety adaptor connector located at the second member second end configured to connect with an external medical device connector or a cable; and
   a safety adaptor conductor extending between the external safety adaptor connector and the breech electrical terminal; and wherein:
   the electrically coupling step further comprises connecting the external safety adaptor connector with an external medical device connector.

30. The method of claim 29, wherein the electrically coupling step further comprises
   locking the first member in the closed position upon connection of the external safety adaptor connector with an external medical device connector to prevent the movement of the first member from the closed position.

31. The method of claim 25, further comprising;
   locking the first member in the closed position upon movement of the first member into the closed position to prevent the movement of the first member from the closed position.

32. The method of claim 25, wherein;
   the inserting step further comprises exposing a portion of the circumference of the at least one lead connector element of the proximal end section of the lead disposed in the elongated bore; and
   the contacting step further comprises engaging the exposed portion of the circumference of the at least one lead connector element of the proximal end section of the lead disposed in the elongated bore against the at least one breech electrical terminal when the first member is moved into the breech.

33. The method of claim 25, wherein:
   the first member comprises an elongated adaptor arm, the first member first end is an adaptor arm free end, the first member second end is an adaptor arm hinged end, and the elongated bore extends between a lead insertion bore end formed in the adaptor arm hinged end and the adaptor arm free end;
   the second member comprises an elongated adaptor body, the second member first end is an adaptor body free end, and the second member second end is a an adaptor body hinged end;
   a hinge connects the adaptor arm hinged end to the adaptor body hinged end; and
   the moving step comprises pivoting the adaptor arm about the hinge from the open position to the closed position such that the elongated adaptor arm is fitted into the breech of the adaptor body.

34. The method of claim 33, wherein the adaptor arm has an adaptor arm length between the adaptor arm hinged end and free end, the adaptor body has an adaptor body length between the adaptor body hinged end and the adaptor body free end, and the breech has a breech length shorter than the adaptor body length and sufficient to receive the adaptor arm length in the closed position such that the free end of the adaptor arm is not exposed in the closed position.

35. The method of claim 33, further comprising:
   locking the adaptor arm in the closed position upon movement of the adaptor arm into the closed position to prevent the movement of the adaptor arm from the closed position.

36. The method of claim 33 particularly adapted for connecting an external medical device to at least one lead connector element of a medical lead extending percutaneously into a patient's body and having a percutaneous penetration needle attached to the lead proximal end, wherein:
   the elongated bore extends through a needle exiting opening of the adaptor arm free end; and
   the inserting step further comprises:
   extending the percutaneous penetration needle through the needle exiting opening upon insertion of the lead proximal end segment into the elongated bore to enable removal of the percutaneous needle; and
   removing the percutaneous penetration needle.

37. The method of claim 33 particularly adapted for connecting an external medical device to at least one lead connector element of a medical lead extending percutaneously into a patient's body and having a percutaneous penetration needle with a weakened zone attached to the lead proximal end, wherein:
   a fulcrum is formed at the adaptor arm free end; and
   the elongated bore extends through a needle exiting opening of the adaptor arm free end; and
   the inserting step further comprises:
   extending the percutaneous penetration needle through the needle exiting opening upon insertion of the lead proximal end segment into the elongated bore to position the weakened zone in working relation with the fulcrum enable removal of the percutaneous needle; and
   removing the percutaneous penetration needle by bending the weakened zone against the fulcrum until the weakened zone breaks.

38. The method of claim 33, wherein the adaptor body further comprises:
   an external safety adaptor connector located at the adaptor body free end configured to connect with an external medical device connector or a cable; and
   a safety adaptor conductor extending between the external safety adaptor connector and the breech electrical terminal; and wherein:
   the electrically coupling step further comprises connecting the external safety adaptor connector with an external medical device connector.

39. The method of claim 38, wherein the electrically coupling step further comprises locking the adaptor arm in the closed position upon connection of the external safety adaptor connector with an external medical device connector to prevent the movement of the adaptor arm from the closed position.

40. The method of claim 33, wherein;
   the inserting step further comprises exposing a portion of the circumference of the at least one lead connector element of the proximal end section of the lead disposed in the elongated bore; and
   the contacting step further comprises engaging the exposed portion of the circumference of the at least one lead connector element of the proximal end section of the lead disposed in the elongated bore against the at least one breech electrical terminal when the adaptor arm is moved into the breech.

41. The method of claim 40, further comprising:

locking the adaptor arm in the closed position upon movement of the adaptor arm into the closed position to prevent the movement of the adaptor arm from the closed position.

42. The method of claim 25, wherein:

the first member comprises an elongated adaptor door having door sides extending between adaptor door first and second ends;

the second member comprises an elongated adaptor body having a door frame surface against which the adaptor door closes in the closed position;

a hinge extends between the adaptor body door frame and an adaptor door side; and the moving step comprises pivoting the adaptor door about the hinge from the open position to the closed position such that the elongated adaptor door is fitted into the breech of the adaptor body and against the door frame surface.

43. The method of claim 42, wherein the adaptor door has an adaptor door length between the adaptor door first end and second end, the adaptor body has an adaptor body length between the adaptor body first end and the adaptor body second end, and the breech has a breech length shorter than the adaptor body length and sufficient to receive the adaptor door length in the closed position such that the second end of the adaptor door is not exposed in the closed position.

44. The method of claim 42, further comprising locking the adaptor door in the closed position upon movement of the adaptor door into the closed position to prevent the movement of the adaptor door from the closed position.

45. The method of claim 42 particularly adapted for connecting an external medical device to at least one lead connector element of a medical lead extending percutaneously into a patient's body and having a percutaneous penetration needle attached to the lead proximal end, wherein:

the elongated bore extends through a needle exiting opening of the adaptor door second end; and the inserting step further comprises:

extending the percutaneous penetration needle through the needle exiting opening upon insertion of the lead proximal end segment into the elongated bore to enable removal of the percutaneous needle; and removing the percutaneous penetration needle.

46. The method of claim 42 particularly adapted for connecting an external medical device to at least one lead connector element of a medical lead extending percutaneously into a patient's body and having a percutaneous penetration needle with a weakened zone attached to the lead proximal end, wherein:

the elongated bore extends through a needle exiting opening of the adaptor door second end;

a fulcrum is formed at the adaptor door second end; and the inserting step further comprises:

extending the percutaneous penetration needle through the needle exiting opening upon insertion of the lead proximal end segment into the elongated bore to the position the weakened zone in working relation with the fulcrum enable removal of the percutaneous needle; and removing the percutaneous penetration needle by bending the weakened zone against the fulcrum until the weakened zone breaks.

47. The method of claim 42, wherein the adaptor body further comprises:

an external safety adaptor connector located at the adaptor body second end configured to connect with an external medical device connector or a cable; and a safety adaptor conductor extending between the external safety adaptor connector and the breech electrical terminal; and wherein:

the electrically coupling step further comprises connecting the external safety adaptor connector with an external medical device connector.

48. The method of claim 47, wherein the electrically coupling step further comprises locking the adaptor arm in the closed position upon connection of the external safety adaptor connector with an external medical device connector to prevent the movement of the adaptor arm from the closed position.

49. The method of claim 42, wherein;

the inserting step further comprises exposing a portion of the circumference of the at least one lead connector element of the proximal end section of the lead disposed in the elongated bore; and the contacting step further comprises engaging the exposed portion of the circumference of the at least one lead connector element of the proximal end section of the lead disposed in the elongated bore against the at least one breech electrical terminal when the adaptor door is moved into the breech.

50. The method of claim 49, further comprising:

locking the adaptor door in the closed position upon movement of the adaptor door into the closed position to prevent the movement of the adaptor door from the closed position.

* * * * *

UNITED STATES PATENT AND TRADEMARK OFFICE
CERTIFICATE OF CORRECTION

PATENT NO. : 6,397,108 B1
APPLICATION NO. : 09/542698
DATED : May 28, 2002
INVENTOR(S) : Camps et al.

It is certified that error appears in the above-identified patent and that said Letters Patent is hereby corrected as shown below:

On title page at (75), delete "Bernardt" and insert --Bernard--.

Signed and Sealed this

Eighteenth Day of July, 2006

JON W. DUDAS
*Director of the United States Patent and Trademark Office*